(12) United States Patent
Verde Sanchez et al.

(10) Patent No.: US 9,168,192 B2
(45) Date of Patent: Oct. 27, 2015

(54) PILLOW FOR THE TREATMENT AND/OR PREVENTION OF CRANIAL DEFORMITIES IN BABIES AND INFANTS

(71) Applicants: David Verde Sanchez, Barcelona (ES); Yin Chern Law, Barcelona (ES)

(72) Inventors: David Verde Sanchez, Barcelona (ES); Yin Chern Law, Barcelona (ES)

( * ) Notice: Subject to any disclaimer, the term of this patent is extended or adjusted under 35 U.S.C. 154(b) by 0 days.

(21) Appl. No.: 14/296,333

(22) Filed: Jun. 4, 2014

(65) Prior Publication Data
US 2014/0352069 A1 Dec. 4, 2014

(30) Foreign Application Priority Data
Jun. 4, 2013 (ES) .................................. 201330825

(51) Int. Cl.
*A61G 7/07* (2006.01)
*A47G 9/10* (2006.01)
*A61F 5/058* (2006.01)

(52) U.S. Cl.
CPC *A61G 7/072* (2013.01); *A47G 9/10* (2013.01); *A61F 5/05891* (2013.01)

(58) Field of Classification Search
CPC ........................................................ A61G 7/07
USPC ...................... 5/630, 636–638, 655
See application file for complete search history.

(56) References Cited

U.S. PATENT DOCUMENTS

| | | | |
|---|---|---|---|
| 3,858,257 A * | 1/1975 | Young | 5/636 |
| 5,367,731 A * | 11/1994 | O'Sullivan | 5/645 |
| 6,052,849 A | 4/2000 | Dixon et al. | |
| 6,539,567 B1 | 4/2003 | Bae | |
| 2006/0042013 A1 | 3/2006 | Madsen | |
| 2007/0256242 A1 | 11/2007 | Warnock | |
| 2010/0180381 A1 | 7/2010 | Verde Sanchez et al. | |

FOREIGN PATENT DOCUMENTS

| | | |
|---|---|---|
| DE | 20-2005-008276 U1 | 8/2005 |
| DE | 10 2009 037159 A1 | 2/2011 |
| ES | 2068518 T3 | 4/1995 |
| ES | 1069689 U | 5/2009 |
| ES | 1070736 U | 10/2009 |
| JP | 2006-068520 A | 3/2006 |
| JP | 2006-239047 A | 9/2006 |

OTHER PUBLICATIONS

The extended European Search Report dated Oct. 7, 2014 of corresponding European Patent Application No. 14382212.0—7 pages.
Search Report dated Apr. 29, 2014, issued in Spanish Application No. 201330825, filed Jun. 4, 2013.

* cited by examiner

*Primary Examiner* — Fredrick Conley
(74) *Attorney, Agent, or Firm* — Knobbe Martens Olson & Bear LLP

(57) ABSTRACT

A pillow for the treatment and/or prevention of cranial deformities in babies and infants, of the type comprising a depression to receive the head, the depression comprising a curved inclined portion located around an opening, which is closed off by a supporting portion for the head of the baby or infant, located at an intermediate height in the pillow, in which the supporting portion comprises a deformable material and the inclined portion forms an angle of more than 130° with the supporting portion in the area where the inclined portion and the supporting portion merge.

16 Claims, 15 Drawing Sheets

PILLOW FOR THE TREATMENT AND/OR PREVENTION OF CRANIAL DEFORMITIES IN BABIES AND INFANTS

CROSS-REFERENCE TO RELATED APPLICATION

This application claims priority to and the benefit of Spanish Patent Application No. 201330825, filed Jun. 4, 2013, which is hereby incorporated by reference in its entirety.

SUMMARY OF THE INVENTION

The present application relates to pillows for the treatment and prevention, or both, of the cranial deformities which may occur during the process of formation and growth of the cranium. The cranium undergoes growth and consolidation processes from birth. Full cranial capacity is achieved at age five. Thus the cranium grows during the periods of breast feeding (babies) and infancy.

Cranial deformations may be of the congenital type, due to disease, or may be postural. In the latter case it is continuing support on an inappropriate surface, with a concentration of pressures on the baby's or infant's head, which gives rise to the deformation because the brain, and therefore the cranium, grows more rapidly in those areas where there is no pressure. The three main deformities produced in this way are known as plagiocephaly, brachycephaly and scaphocephaly.

Various pillows designed to exert a uniform pressure on a baby's cranium to prevent the formation of the abovementioned cranial deformities are known.

Spanish Patent Document ES 1069689U discloses a pillow for the prevention of cranial deformities which is formed of a core of deformable material and a protective fabric covering. The core has a depression or valley to receive the head. This depression ends in an opening. The opening is covered by the protective fabric, the upper and lower layers of which are sewn together around the perimeter of the opening.

Likewise German Patent Publication DE 202005008276 discloses a pillow of fibrous material enclosed by a cover which has an opening to receive the head. The opening is closed off by a membrane sewn to the cover and it is therefore isolated from the material filling the cover. A similar arrangement can be seen in U.S. Pat. No. 6,539,567.

Spanish Patent Document ES 2068518 discloses a therapeutic pillow for adults, which has four lobes, leaving a so-called central "space", independent of the above, which is occupied by a lobe, the highest part of which is of similar height to the rest of the pillow. As a consequence the space in this pillow forms a valley in it. The central lobe is isolated from the others by a reinforcement which provides a boundary for it.

Spanish Patent Document ES 1070736 U discloses a small pillow with a central depression, without an opening, the material forming the pillow beneath the depression being of the same unit as the rest of the parts of the pillow.

U.S Patent Publication US 2006/0042013 A1 discloses a device for positioning a baby's head comprising two wedge-like pieces made of resilient material, the slopes of the wedge join directly by their lowest parts. The slopes of the wedges are straight set as angle of between 0° and 180°. This device can be used for the initial correction of serious cranial deformities. This device, however, is not valid for the treatment of mild cranial deformities, for the continuous treatment of deformities or for the prevention of them. On the contrary, using these devices the baby's head relies on two zones of limited area, which will almost certainly provoke a cranial deformity in healthy babies.

Although known pillows are designed to exert a uniform pressure on a baby's head and it is easy to understand that they exert a more distributed pressure on the head than standard pillows, known pillows do not distribute the pressure in a completely uniform way; neither is it known what shape and size characteristics the central depression should have in order to provide these openings.

The lack of known appropriate pressure measuring instruments, particularly for application to babies' heads (light pressures, small radii of curvature), has made it very difficult to improve existing pillows, which, according to studies made, need to be improved.

One aspect of the present invention is to provide pillows which can distribute the pressure over babies' heads in a uniform way.

Another aspect of the present invention is to provide pillows which are useful in the treatment of existing deformities.

In particular, the present application discloses a pillow for the treatment and prevention of cranial deformities in babies and infants of the type which comprises a depression to receive the head. The depression can include an inclined portion having a curved slope located around an opening that is closed off by a supporting area located at an intermediate height in the pillow. The supporting area can include a deformable material. A sloping portion forms an angle of more than 130° with the supporting area in the portion where the sloping part and the supporting part merge into each other on both sides of the baby's or infant's head.

In some embodiments, the supporting portion has a thickness of between 5 and 9 mm.

In some embodiments, the supporting zone is flat.

In some embodiments, the pillow has an isolating element which isolates the supporting portion from the rest of the pillow.

In some embodiments, the isolating element is a stitched seam.

In some embodiments, the pillow is formed from a core of deformable material located within an enclosing textile sheet. More preferably the core is a foam material. Even more preferably the textile is a three dimensional textile, which also helps to distribute pressure. The three dimensional textile may be a polyester textile.

In some embodiments, the core is formed from a plurality of slices or sheets bonded together and surrounded by an additional outer sheet which encloses them and which extends to the supporting portion mentioned via the seam.

In some embodiments, the angle between the inclined portion and the supporting portion is greater than 135°. Even more preferably the angle between the inclined portion and the supporting portion is 140° or more.

In some embodiments, the inclined portion forms an angle with the supporting portion in the vicinity of the separating element which is equal to or less than 150°.

In some embodiments, the supporting portion is of circular shape and has a diameter of 50 mm or less.

The present application also discloses a pillow of which supporting portion has a circular shape and has a diameter of less than 50 mm and greater than 40 mm.

BRIEF DESCRIPTION OF THE DRAWINGS

For a better understanding, drawings of embodiments of the present invention are provided by way of an explanatory but not limiting example.

DETAILED DESCRIPTION OF THE PREFERRED EMBODIMENT

Figure 1:
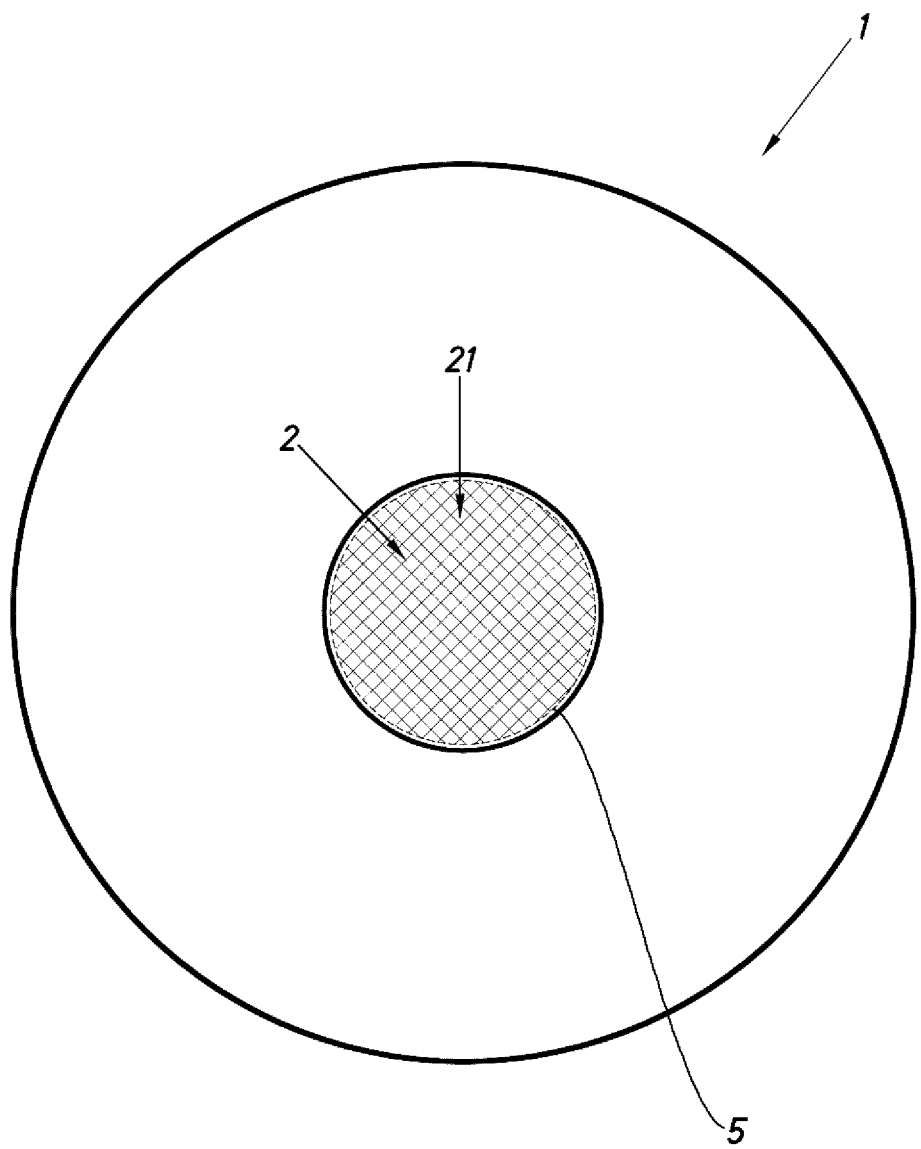
FIG. 1 is a plan view of a pillow for children according to the known art.
Figure 2:
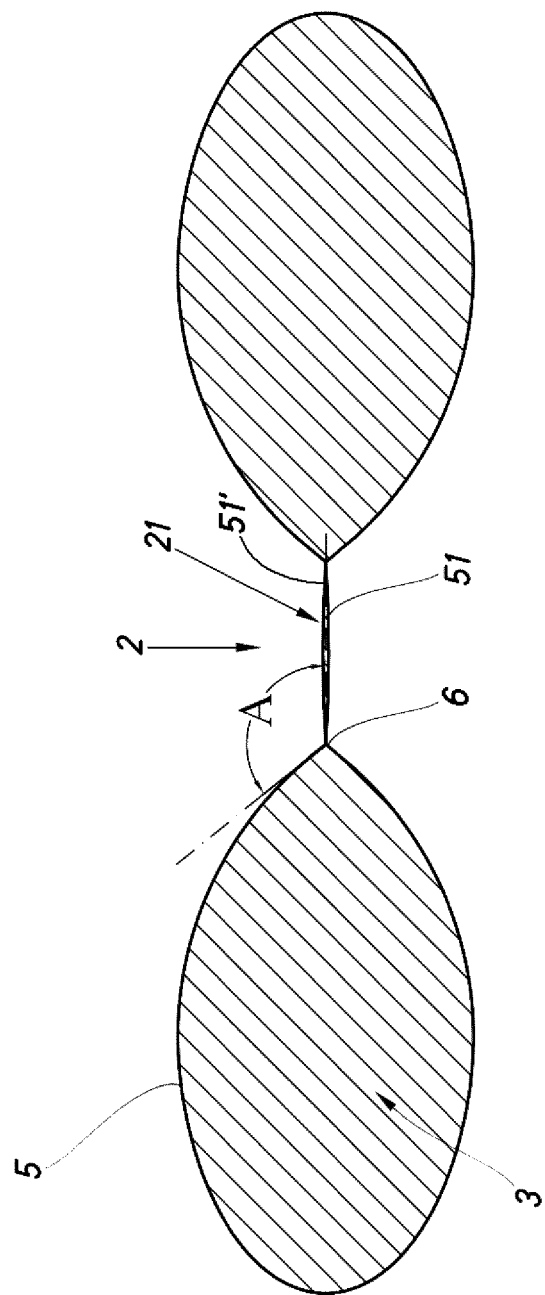
FIG. 2 is a transverse crosssection of the pillow in FIG. 1.

FIGS. 1 and 2 show a known pillow 1 to prevent cranial deformities.

The Known pillow 1 have different shapes (elliptical, circular, square, etc.) with a central opening 2 closed off at midheight by a textile sheet 21. The textile is hanging over a surface on which the pillow lies. The pillow comprises a deformable core 3, made of different materials, which is covered by textile 5.

The membrane covering opening 2 at an intermediate height in the pillow is formed by the upper 51' and lower 51 layers of textile 5 covering core 3. Membrane 51, 51' has a mechanical behaviour which differs from that of the rest of textile 5 covering pillow 1 as a result of a seam 6 which isolates membrane 51', 51 from the rest of textile 5.

As will be seen in FIG. 2, core 3 forms a valley with rounded inclined sides. Angle A which the rounded inclined portion forms with membrane 51, 51' at the junction zone in pillows of the known type is less than 130°, because it is believed that this range of angles assists better discharge of some of the pressure on the posterior part of the cranium. These pillows have not been shown to be effective in correcting existing cranial deformities.

Figure 3:
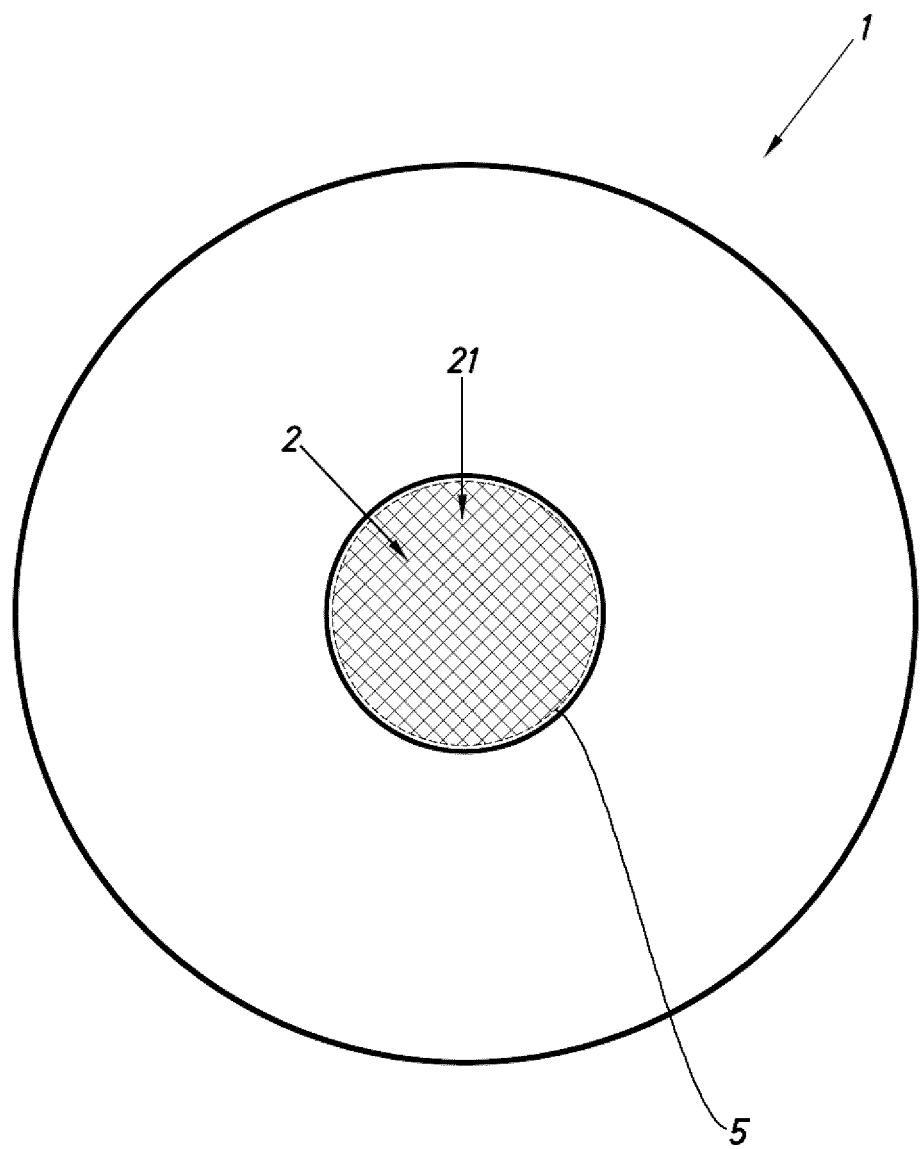
FIG. 3 is a plan view of a pillow according to an embodiment of the present invention.
Figure 4:
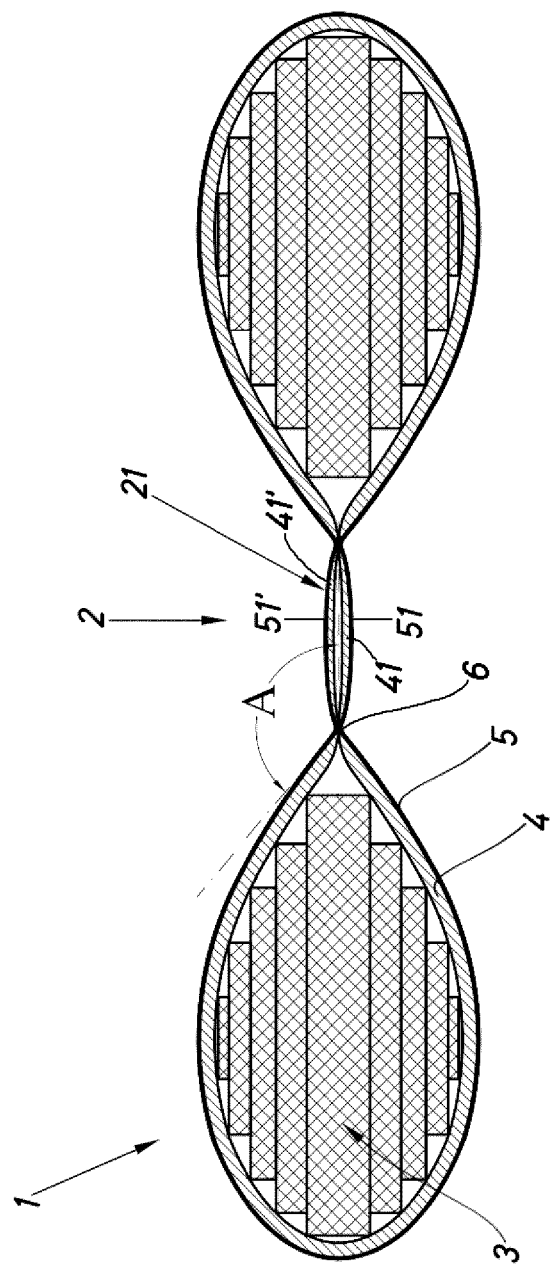
FIG. 4 is a view of a pillow according to an embodiment of the present invention in transverse crosssection.

FIGS. 3 and 4 show a transverse crosssection of a pillow according to an embodiment of the present invention.

The embodiment illustrated has various differences in comparison with a pillow of the known type.

One of these differences is that the membrane 21 covering opening 2 is of deformable material 41, 41'. This deformable material reduces the pressure on the posterior part of a baby's cranium. This is combined with an angle A between the inclined portion and textile sheet 21 which is equal to or greater than 130° for a more suitable distribution of the pressure on the head. The membrane 21 is hanging over the support platform when no pressure is exerted on the pillow. Preferably, the vertical dimensions of the pillow are selected so that the membrane hangs over the surface on which the pillow is supported also when a head is lying on the pillow.

In the embodiment illustrated, deformable core 3 is formed of a series of sheets (slices) of deformable material (for example, foam) bonded to each other and covered by another sheet 4 of deformable material. It is this sheet 4 which connects to opening 2 via the same seam 6 which also isolates the mechanical compartment of the deformable material of opening 2 from core 3. Specifically, the outermost sheet of the core extends to the supporting portion.

The opening 2 can be circular and measures less than 50 mm, or between 40 mm and less than 50 mm.

The structure of the pillow according to an embodiment of the present invention makes it possible to produce pillows having the ability to prevent and also correct cranial deformities in babies and infants of different ages.

Some examples of embodiments are illustrated below.

Example 1

Prevention Pillow for Premature Babies

Angle A: greater than 130° 140°
Diameter of opening 2: 40 mm

Example 2

Prevention Pillow for Babies

Angle A: greater than 140° 150°
Diameter of opening 2: 50 mm

Example 3

Corrective Pillow for Babies Aged Over 5 Months

Angle A: greater than 130° 140°
Diameter of opening 2: 50 mm

Figure 6:
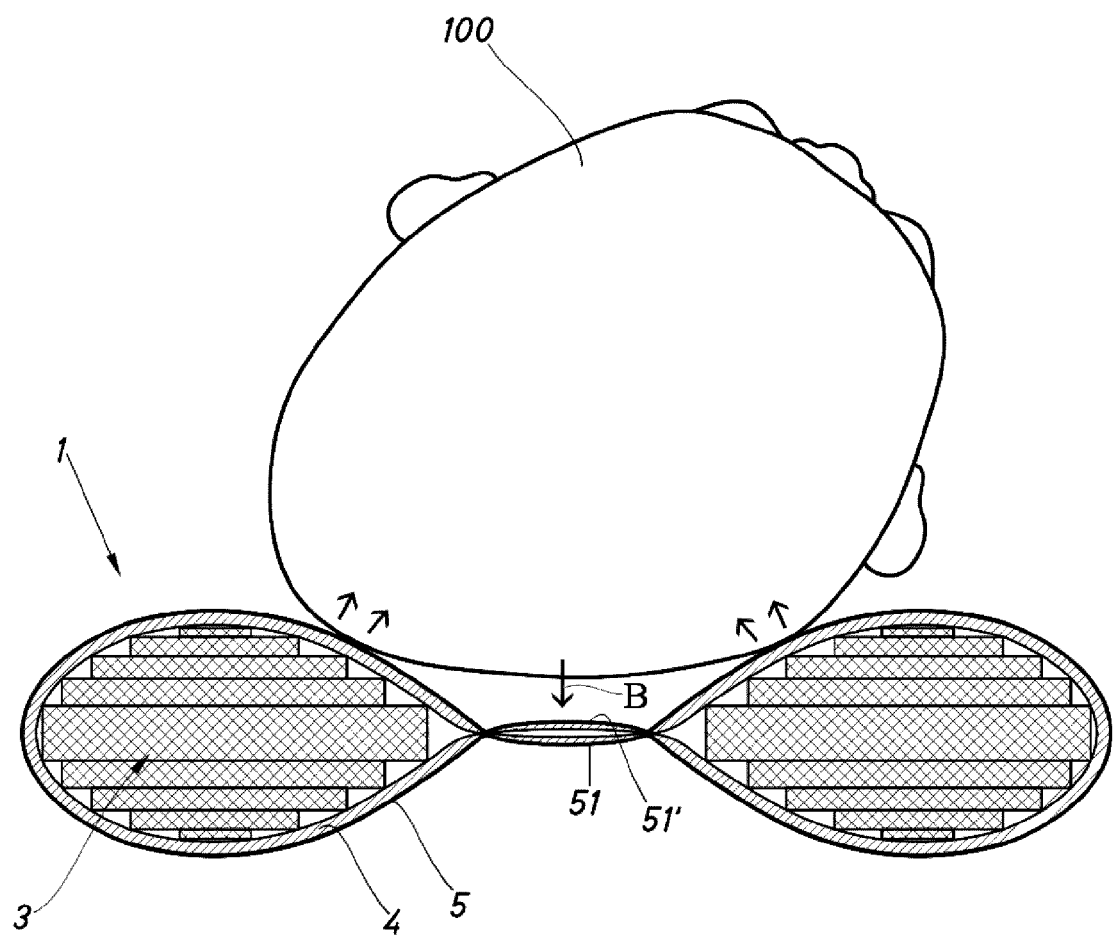
FIG. 6 is a diagrammatical view of the use of a pillow according to an embodiment of the present invention to correct plagiocephaly.
Figure 7:
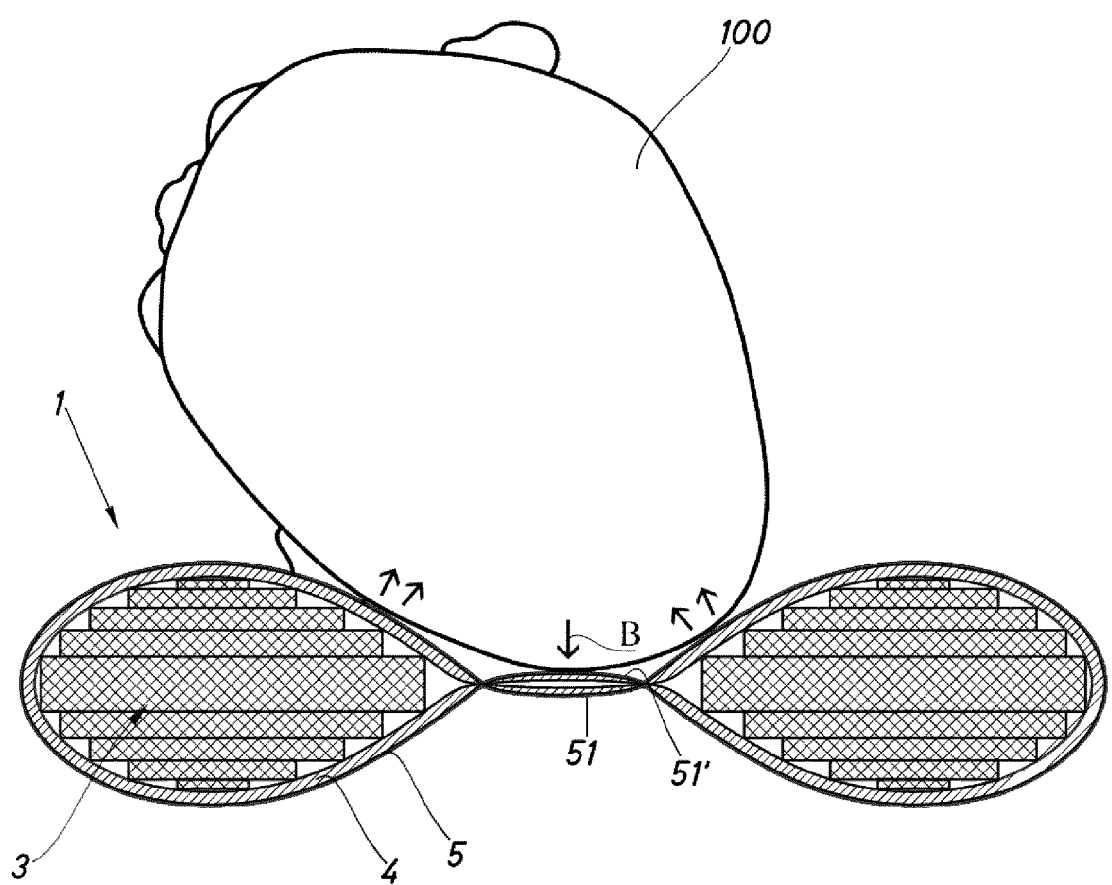
FIG. 7 is a diagrammatical view of the use of a pillow according to an embodiment of the present invention, with the baby placed in a different position.

FIGS. 6 and 7 illustrate a pillow according to an embodiment of the present invention, applied to the correction of plagiocephaly. In FIG. 6, it will be seen how babies/infants experience pressure on the growing portions of the cranium, and none on the flattened portion, when supported on the pillow in the position in which they normally lie (and which has resulted in the occurrence of plagiocephaly as a result of the use of pillows other than those according to an embodiment of the present invention) in such a way that cranial growth in direction B, which is appropriate for this correction, is encouraged. It will be seen how this is brought about by the increased angle A of the pillow according to an embodiment of the present invention. In FIG. 7, it will be seen that this occurs even if the baby rotates its head.

Figure 8:
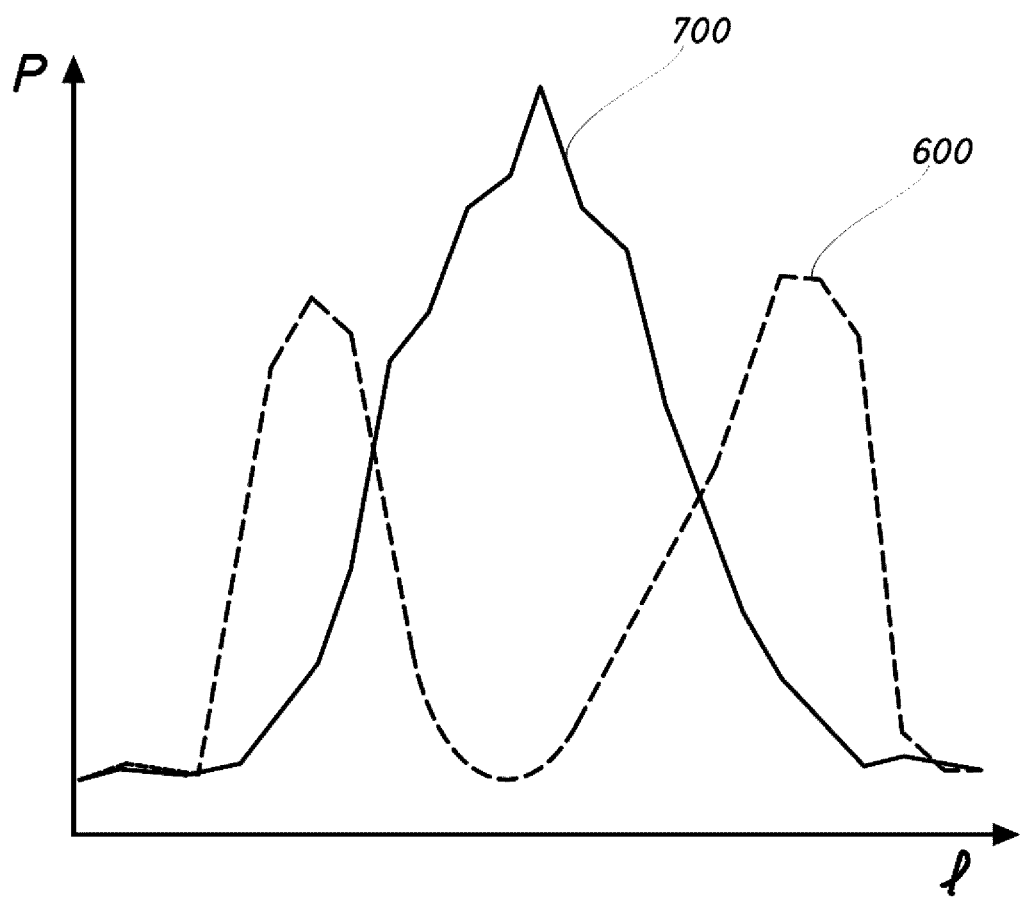
FIG. 8 is a graph showing the pressure exerted by the pillow on the perimeter of a baby's head in the situations illustrated in FIGS. 6 and 7.

FIG. 8 shows development of pressure exerted by a pillow around the circumferential perimeter of a baby's head in the positions illustrated in FIG. 6 (pressure line 600) and FIG. 7 (pressure line 700). It will be seen that the pillow effectively applies greater pressure to the points mentioned earlier, while the pressure on the other portions is a minimum.

To measure pressures in the embodiments illustrated a pressure sensor comprising an arrangement of resilient strips of fabric (76% nylon, 24% elastane) metallised with silver particles, located between two thin sheets of polymer (pp) impregnated with carbon particles, in which this composite is covered by two layers of adhesive vinyl, was used. The conducting elements were separated from each other by at least 2 mm and had a width of at least 4 mm, forming a flexible strip with the ability to bend following the radius of curvature of a baby's head.

The device further comprised a voltagesplitting electrical circuit, connected to a digital analog converter. The device measures pressure by detecting changes in the conductivity of the conductive fabric produced by contact between the polymer and carbon particles, and is sufficiently sensitive as regards the magnitude of the pressure and spatial resolution to analyse the pressures acting on babies' heads.

Figure 9:
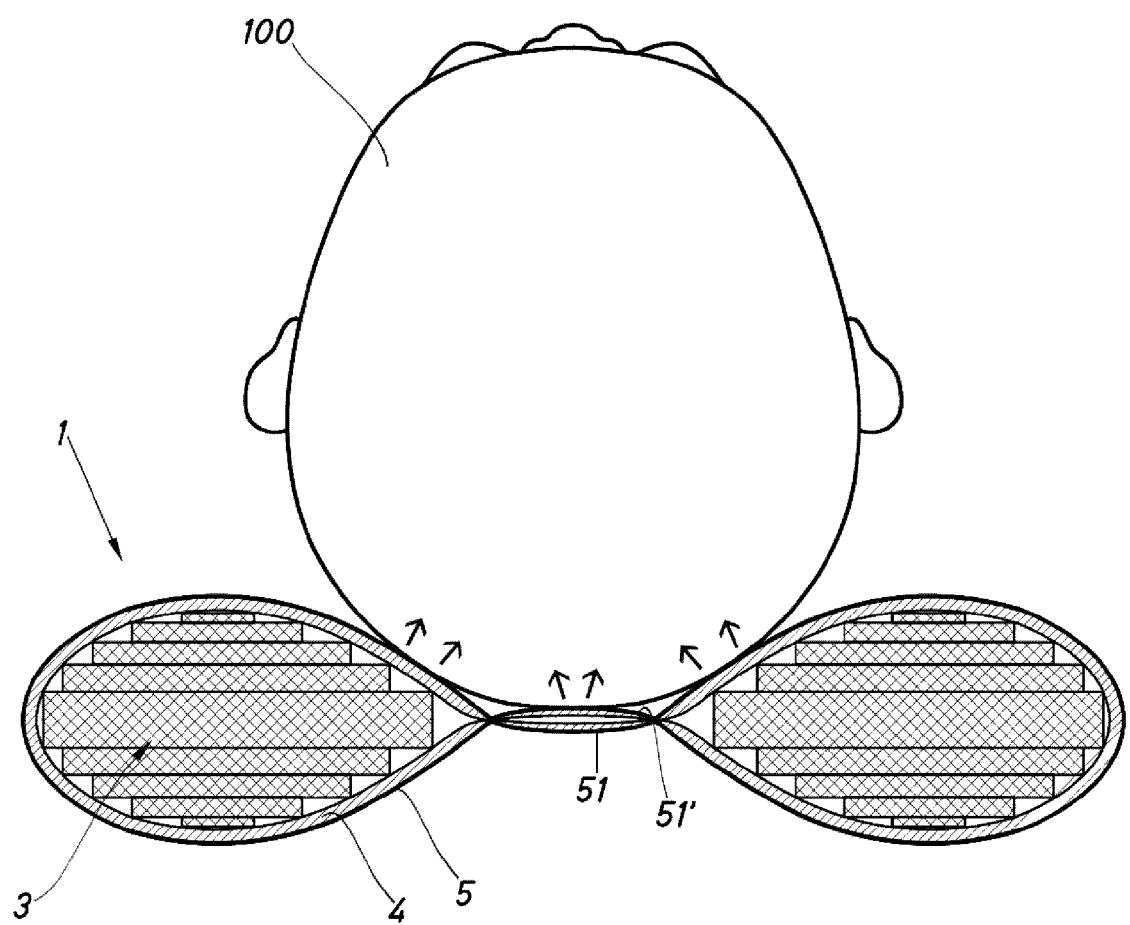
FIG. 9 is a diagrammatical view of the use of a pillow according to an embodiment of the present invention, to prevent deformities in a healthy baby.

FIG. 9 shows a pillow according to an embodiment of the present invention, in its preventive form for a baby having no cranial deformity problems. It will be seen in the figure that the pressure is supported uniformly. In this case the increased angle A according to an embodiment of the present invention helps to provide more uniform distribution, to which the effect of the deformable material covering the opening and the smaller size of the opening (of 50 mm or less) in comparison with other pillows of the known type makes a contribution.

For clarity reasons, FIG. 9 has been represented in a schematic way. In reality, being the pillow made of soft materials and being the supporting portion hanging over the support surface, the pillow contacts all the interior portion of the head and supports it in an uniform way, as the measurements show.

Figure 10:
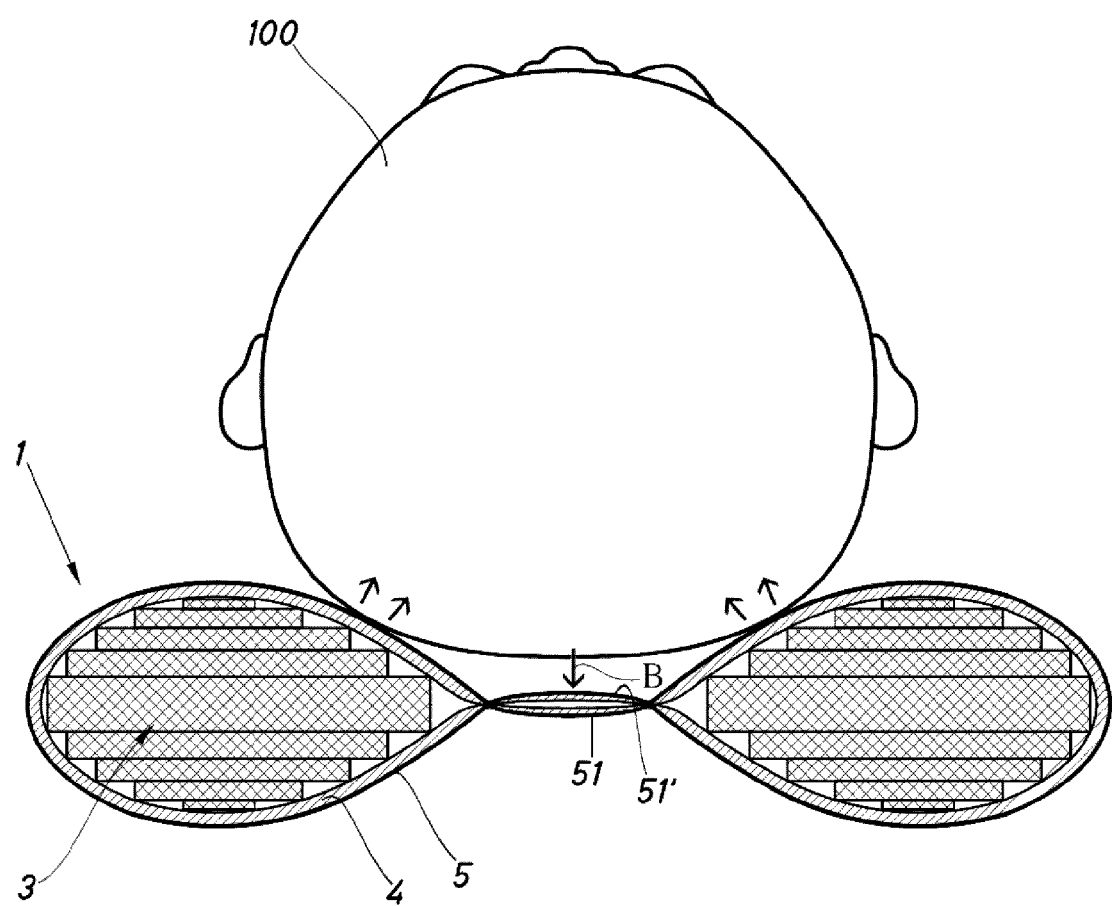
FIG. 10 is a diagrammatical view of the use of a pillow according to an embodiment of the present invention to correct brachycephaly.

FIG. 10 illustrates an embodiment for application to brachycephaly. Here it is important to note that the corrective effect provided by the pillow is complete, because the growth of the cranium is in direction B. It will be seen that, thanks to the pillow having a preventive action in the case of babies without any deformity, the process of correction provided by this pillow is complete and continues to be valid when it enters the preventive phase.

Figure 11:
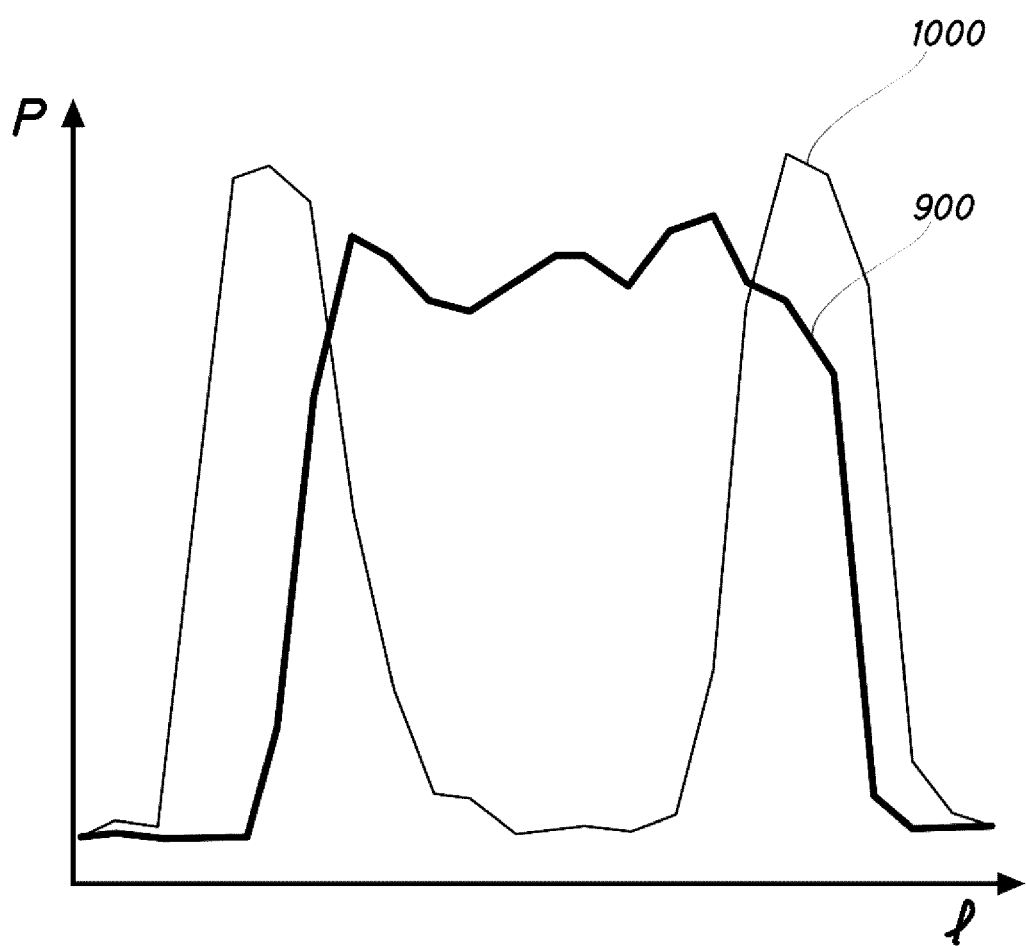
FIG. 11 is a graph showing the pressure exerted by the pillow on the perimeter of a baby's head in the situations illustrated in FIGS. 9 and 10.

FIG. 11 shows the situation around the circumferential perimeter of babies' heads in the circumstances illustrated in FIG. 9 (head without deformity, line 900) and FIG. 10 (brachycephaly, line 1000). As will be seen, in the case where the head is without deformity the pressure is approximately uniform, which prevents the appearance of deformities due to flattening. In the case of brachycephaly it will be seen that there is maximum pressure along line 1000 in the abovementioned portions of the head and minimum pressure in the flattened portions, which will result in correction of the problem.

Figure 12:
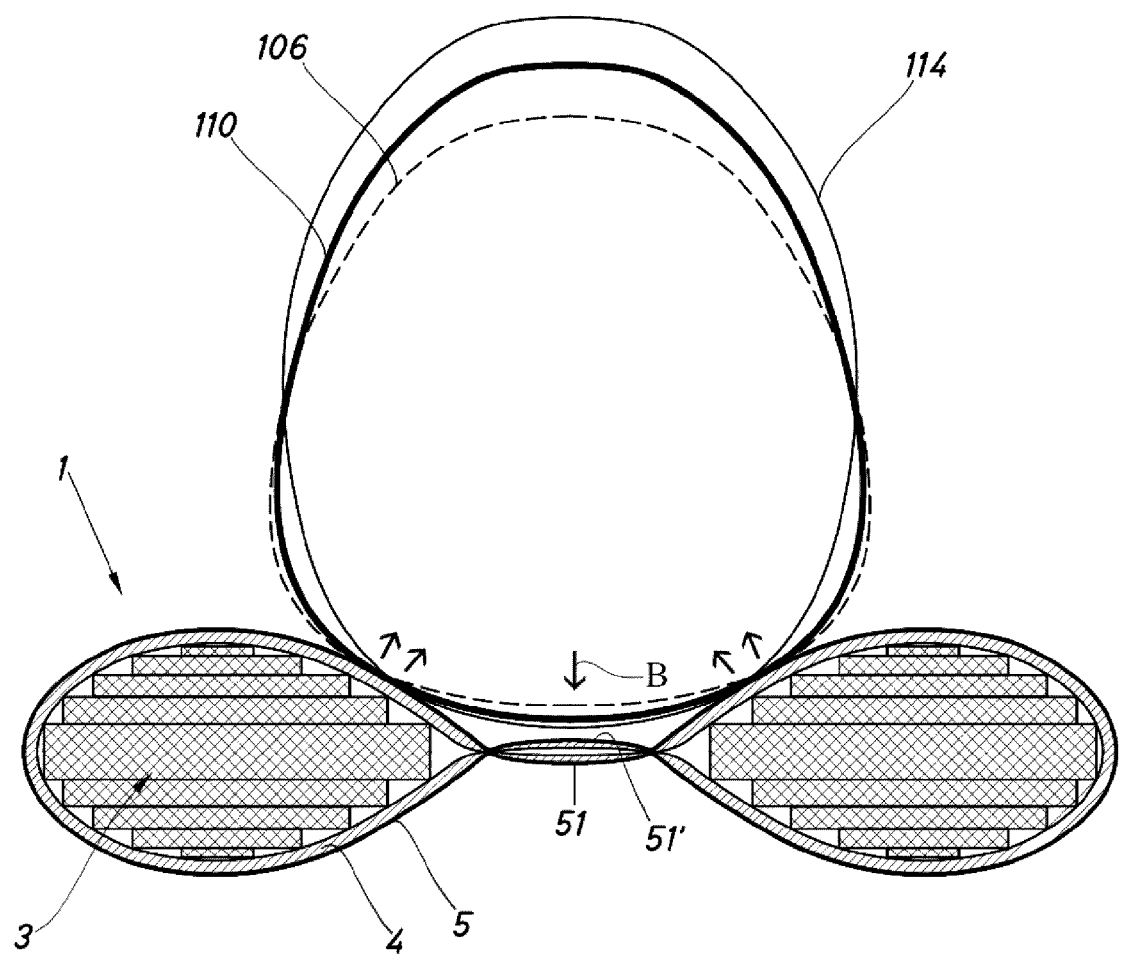
FIG. 12 is a diagram showing the head of a baby who initially had brachycephaly, at three stages of growth. In the last stage the brachycephaly has disappeared.

FIG. 12 shows diagrammatically the change in the force of a pillow, according to an embodiment of the present invention, as a baby's head grows. The figure illustrates the shapes of three heads, 110, 106 and 114 corresponding to an initial brachycephalic stage 106 which is subsequently corrected in subsequent stages 110, 114 as a baby's head grows. In the final stage, baby's head 114 will come into contact with lowermost portion 51, following the line of growth corresponding to arrow B.

Figure 13:
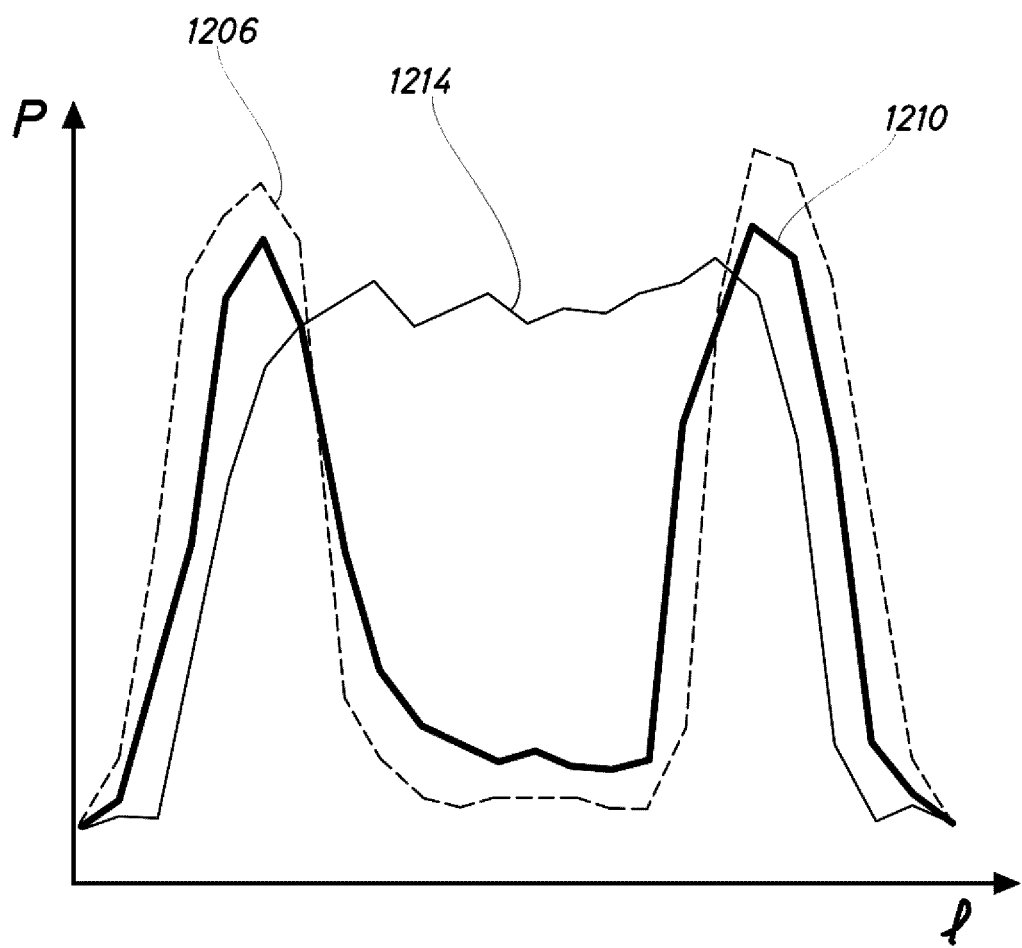
FIG. 13 is a graph showing the pressure exerted by the pillow in the three stages illustrated in FIG. 12.

FIG. 13 provides a graph of the pressure (P) along the longitudinal direction of the baby's head (P) for each of the three stages of growth, pressure line 1206 corresponding to head stage 106, line 1210 to head stage 110 and line 1214 to head stage 114. As will be seen, the corrective pressure peaks are again more marked in the initial stage (pressure line 1206), with the peaks diminishing during subsequent stages, with less cranial deformation (see pressure line 1210), to reach a uniform pressure distribution in the final most deformed state (see pressure 1214).

Figure 5:
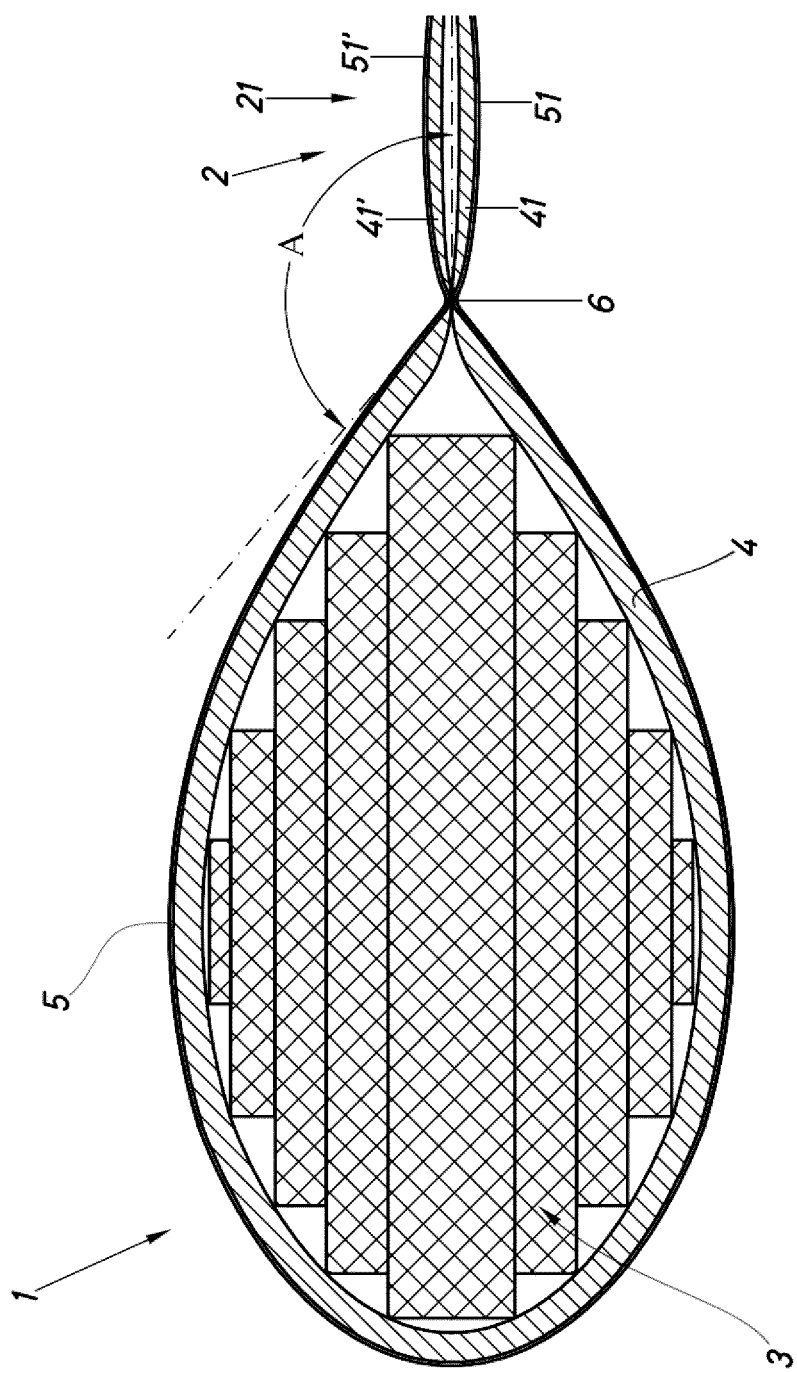
FIG. 5 is a detail of the crosssection in FIG. 3.
Figure 14:
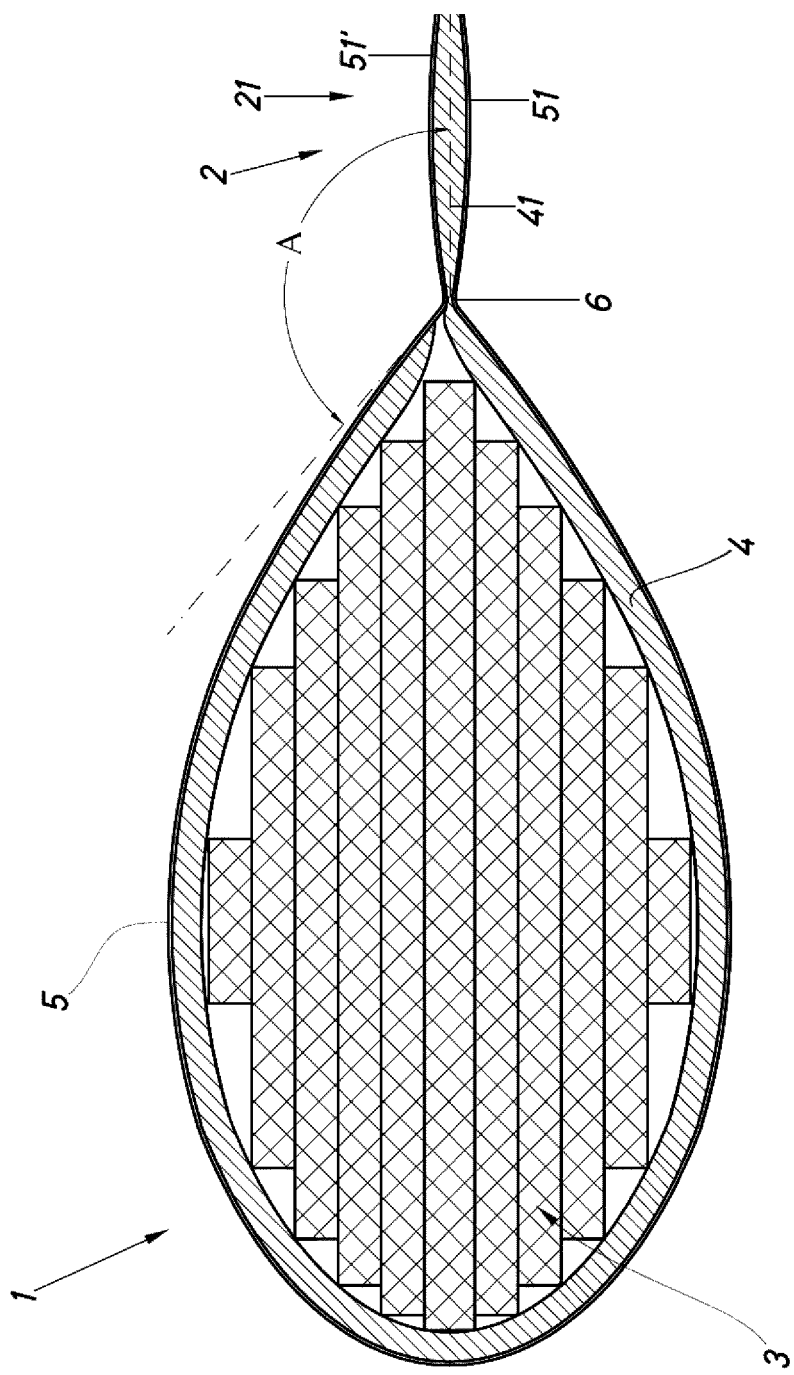
FIG. 14 shows an internal embodiment of the pillow which is an alternative to that illustrated in FIG. 5.

FIG. 14 shows a variant internal construction which is an alternative to that illustrated in FIG. 5. The differences with regard to the crosssection illustrated in FIG. 5 lie in the fact that the differential core 3 is formed by sheets of equal thickness and that sheet 4 of deformable material covering deformable core 3 passes once through opening 2 in such a way that opening 2 is covered by a single layer 41 of deformable material. In this way the portion covering opening 2 is flatter, which is desirable. This is achieved by ensuring that sheet 4 has an end which is embodied in seam 6, without passing from the core portion to the central opening.

Also, if the version illustrated in FIG. 5 or the version illustrated in FIG. 14 is used, the use of a sheet 4 which goes around the entire pillow has the result that the pillow maintains its shape for a longer time during use.

Figure 15:
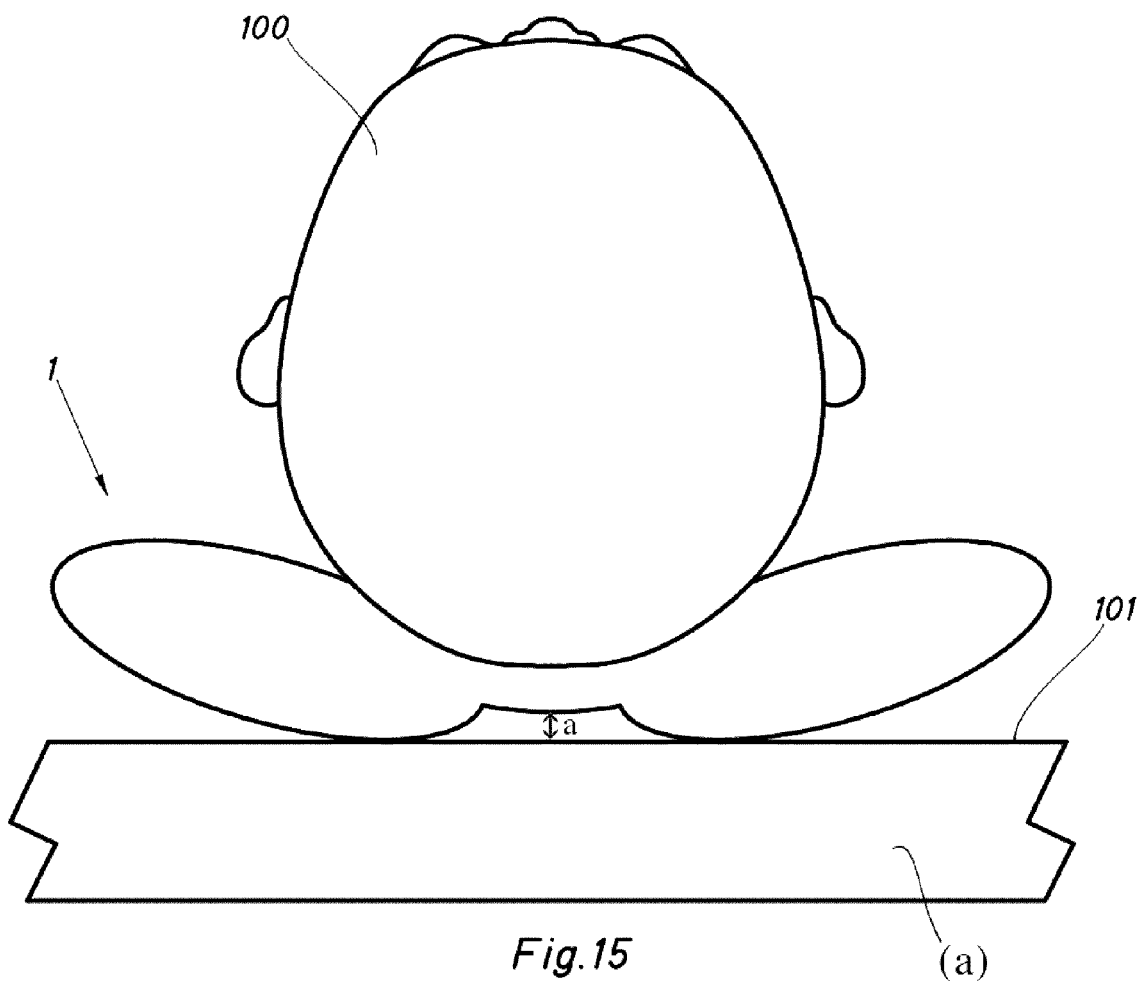
FIG. 15 shows a pillow similar to those of the previous figures in use (the pillow has not been cut off this time).

FIG. 15 shows a pillow 1 similar to those of the previous images in a preferred use. It can be seen how the pillow adapts to the form of the baby head 100. It is also possible to see how the supporting portion hangs over the supporting surface 101, an empty space a being between them. This can be achieved by selecting the initial height of the supporting portion, so that the head weight is not able to completely depress the supporting portion. If the supporting portion is completely depressed by the head, so that it touches the support surface 101, the pressure distribution shown in the previous figures could be modified to varying exents.

Although the invention has been described in relation to some embodiments of the present invention, these should not be regarded as restricting the invention, which will be defined by the broadest interpretation of the following claims.

What is claimed is:

1. A pillow for the treatment and/or prevention of cranial deformities in babies and infants, the pillow comprising:
   a support body that has an opening at center and an inclined portion surrounding the opening, wherein the inclined portion is defined by a deformable core of the support body and a textile covering the deformable core; and
   a support sheet that closes off the opening of the support body,
   wherein the inclined portion of the support body and the support sheet define a depression for receiving and supporting a head of baby infant,
   wherein the deformable core of the support body includes a plurality of deformable layers, and the plurality of deformable layers are stacked on another such that the inclined portion surrounding the opening forms an angle of more than 130° with the support sheet closing the opening.

2. A pillow according to claim 1, wherein the support sheet has a thickness of between 5 and 9 mm.

3. A pillow according to claim 1, wherein the support sheet is substantially flat.

4. A pillow according to claim 1, further comprising an isolating element which isolates the support sheet from the rest of the pillow.

5. A pillow according to claim 4, wherein the isolating element is a sewn seam.

6. A pillow according to claim 1, wherein the dimensions of the pillow are so that the support sheet hangs over a surface on which the pillow lies when a baby or infant head is lying on the pillow.

7. A pillow according to claim 1, wherein the deformable core is of foam material.

8. A pillow according to claim 1, wherein the textile is a three dimensional textile.

9. A pillow according to claim 8, wherein the three dimensional textile is a polyester textile.

10. A pillow according to claim 1, wherein the plurality of deformable layers are bonded together and surrounded by an enclosing outer layer, which extends across the seam in the supporting portion.

11. A pillow, according to claim 1, wherein the angle between the inclined portion and the support sheet is greater than 135°.

12. A pillow according to claim 11, wherein the angle between the inclined portion and the support sheet is 140° or more.

13. A pillow, according to claim 1, wherein the angle between the inclined portion and the support sheet is 150° or less.

14. A pillow, according to claim 1, wherein the central support sheet is of circular shape and has a diameter of 50 mm or less.

15. A pillow according to claim 14, wherein the central support sheet is of circular shape and has a diameter of less than 50 mm.

16. A pillow according to claim 14, wherein the central support sheet is of circular shape and has a diameter of 40 mm or more.

* * * * *